(12) United States Patent
Staats et al.

(10) Patent No.: US 10,739,270 B2
(45) Date of Patent: Aug. 11, 2020

(54) RAPID FIELD TESTING METHOD FOR DETECTING LUBRICANT OR REFRIGERANT ADDITIVES

(71) Applicant: TRANE INTERNATIONAL INC., Davidson, NC (US)

(72) Inventors: Steven Staats, La Crosse, WI (US); Julie A. Majurin, Mindoro, WI (US); Ellis Johnson, River Falls, WI (US)

(73) Assignee: TRANE INTERNATIONAL INC., Davidson, NC (US)

( * ) Notice: Subject to any disclaimer, the term of this patent is extended or adjusted under 35 U.S.C. 154(b) by 366 days.

(21) Appl. No.: 15/665,107

(22) Filed: Jul. 31, 2017

(65) Prior Publication Data
US 2019/0033220 A1  Jan. 31, 2019

(51) Int. Cl.
*G01N 21/78* (2006.01)
*G01N 21/29* (2006.01)
*G01N 31/22* (2006.01)
*G01N 33/28* (2006.01)

(52) U.S. Cl.
CPC .............. *G01N 21/78* (2013.01); *G01N 21/29* (2013.01); *G01N 31/22* (2013.01); *G01N 33/2888* (2013.01)

(58) Field of Classification Search
CPC ........ G01N 21/78; G01N 21/29; G01N 31/22; G01N 33/2888

USPC ........................................................ 436/164
See application file for complete search history.

(56) References Cited

U.S. PATENT DOCUMENTS 5,419,177 A * 5/1995 Pastorello ............ G01N 1/2226
  62/127
5,846,833 A * 12/1998 Clough .............. G01N 33/2835
  436/139
2018/0087815 A1* 3/2018 Kujak .................... F25B 49/005

OTHER PUBLICATIONS

Epstein, J. et al. (1955). "Use of gamma-(4-Nitrobenzyl)pyridine as Analytical Reagent for Ethylenimines and Alkylating Agents." Analytical Chemistry. 27(9). 1435-1439. (Year: 1955).*

* cited by examiner

*Primary Examiner* — Jill A Warden
*Assistant Examiner* — Jacqueline Brazin
(74) *Attorney, Agent, or Firm* — Hamre, Schumann, Mueller & Larson, P.C.

(57) ABSTRACT

A method for operating a field testing device to detect an additive in a refrigerant and/or lubricant. The method includes mixing a reactive medium with the refrigerant and/or lubricant. The reactive medium is configured to react with any additive present in the lubricant and/or refrigerant to form a product that has a different color than the reactive medium. The method also includes determining the additive concentration of the lubricant and/or refrigerant by utilizing the color of the reaction mixture. The field operating device is portable such that the additive concentration may be determined while in the field.

17 Claims, 4 Drawing Sheets

RAPID FIELD TESTING METHOD FOR DETECTING LUBRICANT OR REFRIGERANT ADDITIVES

FIELD

The disclosure relates to testing equipment and testing methods to test for additives in a refrigerant or lubricant.

BACKGROUND

A heating, ventilation, air conditioning, and refrigeration ("HVACR") system and other refrigeration systems cool and/or heat a fluid utilizing a working fluid. A HVACR or refrigeration system utilizes a refrigerant and/or refrigerant mixture as a working fluid. Lubricants provide lubrication for a variety of different types of mechanical devices and have a multitude of applications. For example, a lubricant may be used in the compressor of a HVACR system. During operation of the HVACR or refrigeration system, some of the lubricant may mix with the working fluid. One or more additives may be added to a refrigerant or a lubricant to improve a quality of a refrigerant or lubricant. The additive may provide, for example, additional chemical stability to the refrigerant or lubricant.

SUMMARY

Lubricants and refrigerants can include one or more additives. The amount or concentration of additive(s) in a lubricant or refrigerant may affect its performance. A field technician may need to test a lubricant and/or refrigerant to determine the concentration of an additive in the lubricant and/or refrigerant. Described herein are embodiments of a method for determining the concentration of an additive in a sample of lubricant or refrigerant. In some embodiments, a method allows the operator to visually determine the concentration of the additive. The method allows an operator (e.g., a field technician) to quickly and accurately test a sample of lubricant or refrigerant in the field (e.g., at or near the refrigeration system). Also described herein is a field testing device that allows an operator (e.g., a field technician) to accurately and quickly determine the concentration of an additive in a lubricant or refrigerant in the field.

Disclosed is an embodiment for a method for detecting an additive in a refrigerant, a lubricant, or combination thereof. The method includes mixing a lubricant and/or a refrigerant with a reactive medium. If the lubricant and/or refrigerant include an additive, the reactive medium reacts with the additive to form a product with a different color than the reactive medium. The method also includes determining a color of the reaction mixture, the reaction mixture including one or more of the product and the reactive medium. The color of the reaction mixture is then used to determine an additive concentration of the lubricant and/or refrigerant. In an embodiment, a field testing device may be operated according to the disclosed method. The field testing device is portable such that the method can be carried out in the field (e.g., at or near the refrigeration system that needs to be tested).

Also disclosed is an embodiment for a field testing device for detecting an additive in a refrigerant, a lubricant, or combination thereof. The field testing device has a vessel for testing a lubricant and/or refrigerant. The field testing device also includes a reactive medium that reacts to an additive in the refrigerant and/or lubricant to form a product. The color of the produced reaction mixture corresponds to and can be used to determine an additive concentration of the refrigerant and/or lubricant.

BRIEF DESCRIPTION OF THE DRAWINGS

Both described and other features, aspects, and advantages of the method for detecting an additive in a refrigerant, a lubricant, or combination thereof or the field testing device will be better understood with reference to the following drawings.

DETAILED DESCRIPTION

Figure 1:
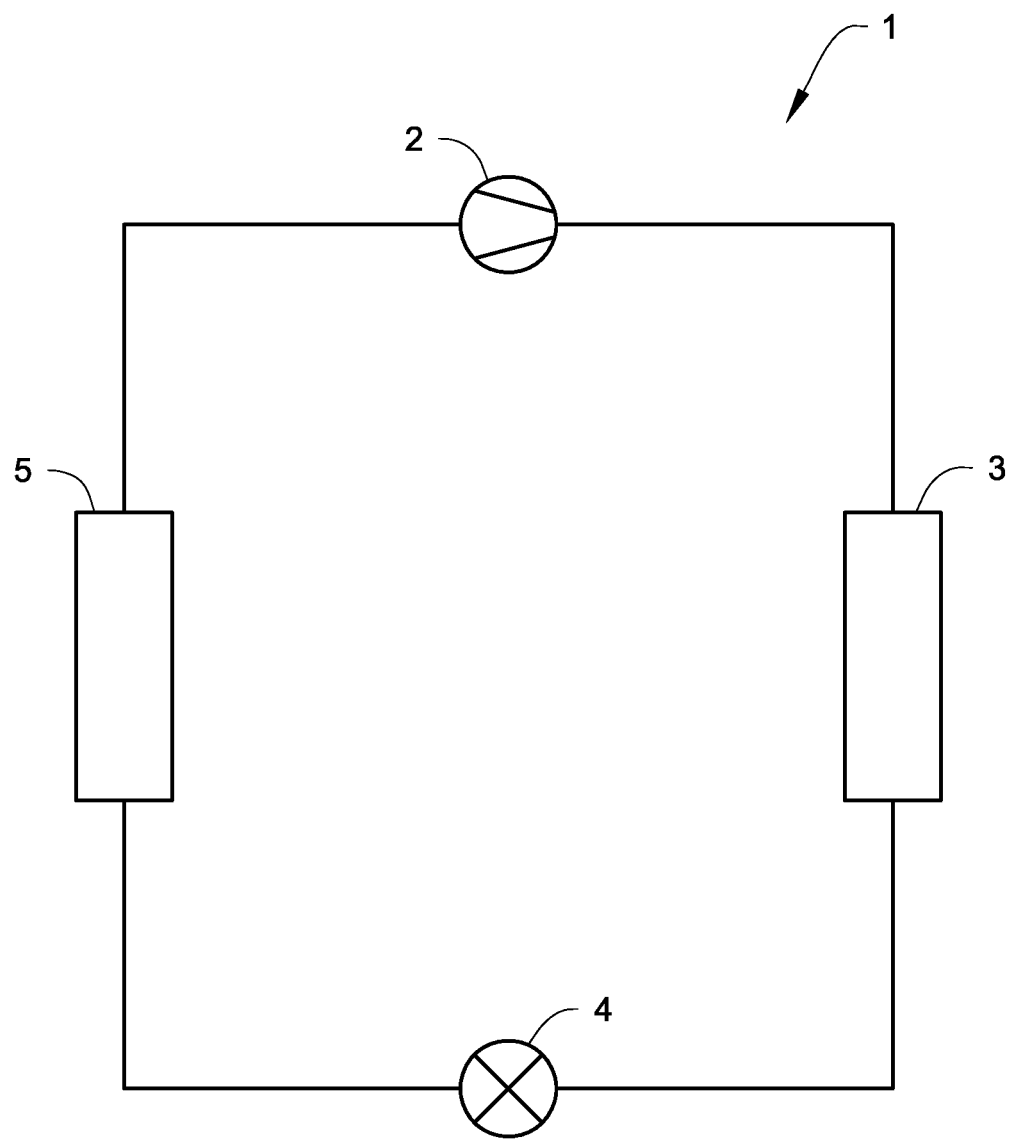
FIG. 1 shows a schematic diagram of a heat transfer circuit in an embodiment.

Lubricants and refrigerants in an HVACR system or other refrigeration systems can include an additive to enhance their performance. A lubricant or refrigerant can include a certain amount of an additive (e.g. a minimum concentration) for the additive to be effective. An additive is effective when it is able to provide a specific property (e.g., additional chemical stability) to the lubricant or refrigerant. An additive may only comprise a small portion of the refrigerant and/or lubricant. Additives are added in relatively low concentrations so as to prevent (or at least reduce) any negative effect the additive may have on the overall performance of the lubricant and/or refrigerant. In an embodiment, the minimum concentration of additive may be an amount as suitable and/or desired for the additive to provide beneficial properties (e.g., enhanced chemical stability) to the lubricant and/or refrigerant. For example, the minimum concentration of additive in a lubricant and/or refrigerant may be an amount between 50 parts per million ("ppm") by weight and 3000 ppm by weight. In an embodiment, the minimum concentration of additive of a lubricant and/or refrigerant may be, for example, at or about 50 ppm by weight, at or about 1000 ppm by weight, or at or about 3000 ppm by weight. It should be understood that a refrigerant may refer to a single chemical or a mixture of chemical components. It should be understood that a lubricant may refer to a single chemical or a mixture of chemical components.

A lubricant is provided in HVACR systems in various mechanical components. For example, a compressor in a HVACR system may require a lubricant. In an embodiment, a lubricant may be, for example, a polyolester oil, an alkylbenzene oil, or a blend of a polyolester oil and alkylbenzene oil. One or more additives may be provided in a lubricant. Additives can be any chemical that can enhance the performance or reliability of the resulting lubricant mixture. For example, an additive for a lubricant in an embodiment may be one or more of an antioxidant, a pressure agent, an antifoam, or a stabilizer.

Previously, refrigerants have not typically required additives. However, new refrigerant or refrigerant mixtures are being developed. In some instances, refrigerants are being developed to meet new environmental and regulatory regulations. A refrigerant may be, for example, a mixture including one or more hydrofluorocarbons ("HFC") and/or a mixture including one or more hydrochlorofluorocarbons ("HCFC"). For example, stabilizers are being added to these refrigerants to provide enhanced chemical stability during handling and/or operation. A stabilizer for a refrigerant and/or a lubricant may be an acid scavenger. One or more epoxides may be added to a refrigerant and/or lubricant as acid scavengers. An epoxide that is an acid scavenger may be, for example, ethylene oxide and/or butylene oxide. An epoxide that is an acid scavenger may also be, for example, a chemical compound that has one or more epoxide groups. The epoxide functions as acid scavenger by undergoing a ring-opening reaction with strong acids (e.g., hydrochloric acid). The ring-opening reaction between the epoxide and the strong acid neutralizes the strong acid.

A stabilizer for a refrigerant and/or a lubricant may be a molecular stabilizer. One or more hydrazones may be added to a refrigerant and/or lubricant to provide molecular stability.

Additives can be difficult to detect due to their low concentration and/or chemical composition. Chromatography and mass-spectrometry has been used to determine the amount of additive(s) in a lubricant or refrigerant. In particular cases, highly sensitive testing equipment such as a gas chromatograph-mass spectrometer has been required to determine the epoxide concentration of a lubricant and/or refrigerant. Both chromatography and mass-spectrometry require a laboratory setting. Accordingly, a sample of a lubricant and/or refrigerant had to be sent to a laboratory to determine its additive concentration. This laboratory based analysis requires knowledgeable operators and high-end equipment. Significant delay can occur between sample collection and a determination of an additive concentration of a sample as the sample had to be sent to a testing facility (e.g., a laboratory) for analysis, which is remotely located relative to where the refrigeration system (e.g., a HVACR system) is located (e.g., the location where the refrigeration system is operated). The analysis of the sample also requires additional time. If additional additive(s) need to be added, this delay would require a field technician to travel back to the refrigeration system to add additional additive(s). The laboratory based analysis and possible additional time spent by a technician incur additional costs.

Some embodiments described herein are directed to a testing method that allows an operator (e.g., a field technician) to quickly and accurately test a refrigerant and/or lubricant sample to determine its additive concentration. The method allows for a refrigerant and/or lubricant to be tested at the subject equipment (e.g., a HVACR system) in the field (e.g., at or close to the building with subject equipment) without requiring a sample to be sent to a remote location for laboratory based analysis. In some embodiments, the testing method is a visual testing method that does not require additional testing equipment other than the reactive medium and a vessel to test the sample.

Some embodiments described herein are directed to a field testing device that allows an operator (e.g., a field technician) to quickly and accurately perform a test on a lubricant and/or refrigerant for an additive concentration. The method and field testing device allow for testing of a lubricant and/or refrigerant without needing a sample to be sent to a remote location (e.g., a testing laboratory).

An HVACR system can be used to cool or heat one or more conditioned spaces. An HVACR system may utilize a working fluid (e.g., a refrigerant) in a circuit to cool a process fluid (e.g., air, water). For example, an HVACR system in some instances will cool an area by performing work on a refrigerant that is in a heat exchange relationship with air. The cooled air may then be ventilated to an area to cool the area.

FIG. 1 is a schematic diagram of an embodiment of a heat transfer circuit 1. The heat transfer circuit 1 can be applied to a variety of systems (e.g., a vapor compression system) to control an environmental condition (e.g., temperature, humidity, air quality) in a space. This space is typically referred to as a conditioned space. Exemplary systems that include a heat transfer circuit 1 include, but are not limited to, HVACR systems, transportation systems, and the like.

As shown in FIG. 1, the heat transfer circuit 1 generally includes a compressor 2, a condenser 3, an expansion device 4, and an evaporator 5. In an embodiment, the heat transfer circuit 1 can be modified to include additional components. For example, in an embodiment, the heat transfer circuit 1 can include an economizer heat exchanger, one or more flow control devices, a receiver tank, a dryer, a suction-liquid heat exchanger, or the like.

The components of the heat transfer circuit 1 are fluidly connected. The heat transfer circuit 1 can be configured as a cooling system (e.g., a fluid chiller of an HVACR, an air conditioning system, and the like) that can be operated in a cooling mode. Alternatively, the heat transfer circuit 1 can be configured to operate as a heat pump system that can run in a cooling mode and a heating/defrost mode.

The heat transfer circuit 1 as described applies known principles of gas compression and cooling. The heat transfer circuit 1 can be configured to heat or cool a process fluid (e.g., water, air). In an embodiment, the heat transfer circuit 1 may represent a chiller that cools a process fluid such as water or the like. In an embodiment, the heat transfer circuit 1 may represent an air conditioner or heat pump that includes a process fluid such as air or the like.

During the operation of the heat transfer circuit 1, a working fluid (e.g., refrigerant) flows into the compressor 2 from the evaporator 5 at a relatively lower pressure in a mostly gaseous state. The compressor 2 compresses the mostly gaseous working fluid into a high pressure state, which also heats the gas. After being compressed, the relatively higher pressure and higher temperature gaseous working fluid flows from the compressor 2 to the condenser 3. In addition to the refrigerant flowing through the condenser 3, an external fluid (e.g., external air, external water, chiller water, and the like) also flows through the condenser 3. In accordance with known principles, the external fluid absorbs the heat from the working fluid as it flows through the condenser 3 turning liquid. The mostly liquid working fluid then flows into the expansion device 4. The expansion device 4 reduces the pressure of the working fluid. The reduced pressure allows the working fluid to expand and be converted to a mixed vapor/liquid state. The relatively lower temperature, vapor/liquid working fluid then flows into the evaporator 5. A process fluid (e.g., air, water, and the like) also flows through the evaporator 5. In accordance with known principles, the working fluid absorbs heat from the process fluid as it flows through the evaporator 5. As the working fluid absorbs heat, the working fluid becomes mostly gaseous. The mostly gaseous working fluid then returns to the compressor 2. The above-described process occurs while the heat transfer circuit 1 is operated, for example, in a cooling mode.

The refrigerant utilized by the heat transfer circuit 1 includes an additive to enhance the performance of the refrigerant. Mechanical equipment (e.g., compressor 2) may also require a lubricant that may include an additive to enhance performance of the lubricant. For example, an additive (e.g., an epoxide, a hydrazone) may be added to the refrigerant or lubricant as a stabilizer that provides enhanced chemical stability. A minimum concentration of the additive may be needed to provide the refrigerant and/or lubricant with the suitable and/or desired chemical stability, as discussed above. During operation, some lubricant may mix with the working fluid as it flows through, for example, the mechanical equipment. Further, the heat transfer circuit 1 in an embodiment may also include an oil separator (not shown) that separates the lubricant from the working fluid (e.g., refrigerant).

Figure 2:
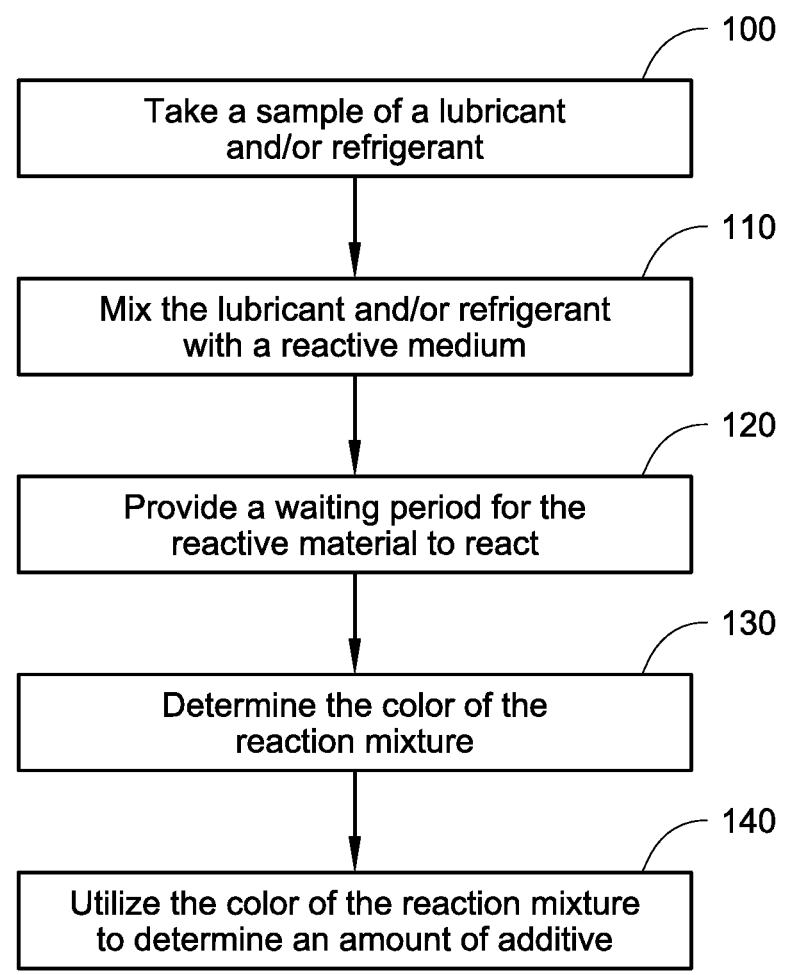
FIG. 2 shows an embodiment of a method for detecting an additive in a refrigerant and/or lubricant.

FIG. 2 illustrates an embodiment of a method of detecting an additive. A refrigerant and/or lubricant include an additive, as described above. A sample of lubricant and/or refrigerant is taken from a refrigeration system (e.g., heat transfer circuit 1, HVACR system) at step 100. In an embodiment, a sample of refrigerant may be taken from various locations along the refrigeration system. For example, a field technician may procure a sample of the refrigerant from one of the various components (e.g., compressor 2, condenser 3, expansion valve 4, evaporator 5 shown in FIG. 1) of the refrigeration system or at a location between the various components (e.g., along the fluid lines or at other components). The location is selected so that a liquid sample of refrigerant and/or lubricant may be taken. For example, a field technician may procure a sample of the lubricant from a component (e.g., compressor 2) that specifically utilizes the lubricant. As described above, during operation, some lubricant may mix with the working fluid in a refrigeration system. Thus, in an embodiment, a sample of the working fluid of the refrigeration system may include refrigerant or refrigerant and lubricant.

During operation, additive(s) may not be equally distributed throughout the refrigeration system (e.g., heat transfer circuit 1). The working fluid may have a higher concentration in a specific component (e.g., compressor 2, condenser 3, expansion valve 4, and evaporator 5 in FIG. 1) relative to the average concentration of the entire refrigeration system or other components. This may occur, for example, as a result of the additive having a low boiling point. In an embodiment, the temperature of the working fluid may be higher in the condenser 3 than in the evaporator 5. As such, the condenser 3 may have a lower concentration of additive(s) and the evaporator 5 may have a higher concentration of additive(s) in an embodiment.

The sample is then mixed with a reactive medium at step 110. The reactive medium is a substance (e.g., chemical compound) that reacts with the additive to form a product. The product has a different color than the color of the reactive medium. For example, in an embodiment, the reactive medium may be colorless (e.g., transparent, mostly transparent) and the product may be yellow. In an embodiment, the reactive medium may be yellow and the product may be colorless. In an embodiment, the reactive medium and the product may be a specific color (e.g., yellow, orange, blue, red, violet, white, pink) instead of one being colorless. It should be appreciated that color may refer to the color type (e.g., blue, red, violet, white), the intensity of a color type, or a light reflecting property. For example, in an embodiment, the reactive medium and the product may be the same color type, but each has a different intensity of the color type. A light reflecting property refers to how a material interacts with light in the visible and/or non-visible spectrums. For example, in an embodiment, the reactive medium and the product may reflect a different amount (e.g., percentage) of a specific wavelength of light. The specific wavelength of light may include wavelengths in the non-visible light spectrum (e.g., the ultraviolet spectrum, the infrared spectrum).

In an embodiment, the lubricant and/or refrigerant include an epoxide as an additive and the reactive medium is or includes hexavalent chromium (e.g., chromium (VI)). The hexavalent chromium reacts with the epoxide to form a chromium (III) complex. The chromium (III) complex has a different color (e.g., white/colorless) than the reactive medium (e.g., yellow).

In an embodiment, the lubricant and/or refrigerant include an epoxide as an additive and the reactive medium reacts with the epoxide to form a quinone. The reaction of the reactive medium and the epoxide may include two separate reactions in an embodiment. In such an embodiment, the reactive medium includes a first reactant and a second reactant. When a sample (e.g., a lubricant and/or refrigerant sample) is mixed with the reactive medium, the epoxide reacts with the first reactant to form an aldehyde. The aldehyde is an intermediate. The second reactant then reacts with the aldehyde to form the quinone. The first reactant may be a Lewis acid such as, for example, boron trifluoride ($BF_3$), aluminum fluoride ($AlF_3$), and/or ammonia ($NH_3$) in an embodiment. The second reactant may be, for example, sulfuric acid and xylene in an embodiment. The quinone has a different color (e.g., pink) than the reactive medium (e.g., white).

In an embodiment, the lubricant and/or refrigerant include an epoxide as an additive and the reactive medium reacts with the epoxide to form a liquid colored product. The reaction of the reactive medium and the epoxide may include two separate reactions in an embodiment. In such an embodiment, the reactive medium includes a first reactant and a second reactant. In an embodiment, the first reactant is 4-(p-nitrobenzyl)-pyridine and the second reactant is potassium acid phthalate. The epoxide reacts with the 4-(p-nitrobenzyl)-pyridine and the potassium acid phthalate to form a colored (e.g., orange) product.

In an embodiment, the lubricant and/or refrigerant include a hydrazone as an additive and the reactive medium reacts with the hydrazone to form a colored (e.g., violet) product. The reaction of the reactive medium and the epoxide may include two separate reactions in an embodiment. In such an embodiment, the reactive medium includes a first reactant and a second reactant. When the lubricant and/or refrigerant is mixed the reactive medium, first reactive reacts (e.g., hydrolyze) with the hydrazone to form a hydrazine. The second reactant may then react with the hydrazine to form a product. The first reactant may be a substance (e.g., chemical compound) that can hydrolyze a hydrazone to form a hydrazine. For example, the first reactant may be a weak organic acid that can hydrolyze the additive hydrazone in the lubricant and/or refrigerant mixture to form a hydrazine. A weak organic acid may have, for example, a pH equal to or greater than 3 and less than 7. The second reactant may be, for example, an alkali and a saliclaldehyde in an embodiment.

The reactive medium and the additive may require a longer period to react in an embodiment. Thus, the method in an embodiment may include a waiting period at step 120. The waiting period allows the reactive medium and the additive to react. In an embodiment, the reactive medium is not completely consumed during the waiting period. In an embodiment that includes two or more reactions, the waiting period may be based on the reaction rates of one or more of the reactions. In an embodiment, the waiting period may be, for example, up to 1 minute, up to 10 minutes, up to 15 minutes, at or about 1 minute, at or about 10 minutes, at or about 15 minutes, at or about 1 minute to at or about 10 minutes, at or about 1 minute to at or about 15 minutes, at or about 10 minutes to at or about 15 minutes.

A color of the reaction mixture is then determined at step 130. The reaction mixture includes the reactive medium, the product formed by the reaction of the additive and the reactive medium, or combination thereof. In an embodiment, the product may be a liquid. A lubricant and/or refrigerant can mix with the product as it forms, which can dilute the color of the product. In such an embodiment, the reaction mixture may include the lubricant and/or refrigerant as the product is mixed with the lubricant and/or refrigerant. In an embodiment, the color of the reactive medium is determined (e.g., step 130) at a specific time after mixing the reactive medium and the additive (e.g., step 110). This specific time in an embodiment may be the length of the waiting period of step 120. In an embodiment, the product has a different color (e.g. color type, color intensity, light reflecting property) than the reactive medium. Accordingly, the color of the reaction mixture changes based on the amount of product formed and the product's color. If the lubricant does not have enough additive, the color of the product may not be visually perceivable.

A light reflecting property of the reaction mixture is the amount (e.g., percentage) of light that that the reaction mixture reflects when the light is at a specific frequency (e.g., wavelength). For example, in an embodiment, a light reflecting property may be the percentage of a 327 nm wavelength light reflected by the reaction mixture. However, the particular light reflecting property in an embodiment may be selected as suitable and/or desired based on the reflective properties of the reactive medium, product, and lubricant and/or refrigerant. The light reflecting property in an embodiment may be selected so that the amount of light reflected by the reaction mixture is a function of the amount of product in the reaction mixture. For example, the reaction mixture may reflect a greater amount of 327 nm wavelength light as the reactive mixture contains a greater amount of product. In an embodiment, color may be a determination of one or more light reflecting properties of the reaction mixture. For example, in an embodiment, a spectrophotometer may be used to determine the light reflecting property of the reaction mixture at step 130. A portable (e.g., a handheld) spectrophotometer may be used to determine the light reflecting property or properties of the reaction mixture. As a spectrophotometer can be easily portable (e.g., small enough to be easily carried in the field), a field technician can easily and quickly test the lubricant and/or refrigerant sample.

The color of the reaction mixture is utilized to determine the amount of additive (e.g., a concentration) in the refrigerant and/or lubricant at step 140. As the product has a different color than the reactive medium, the color of the reaction mixture changes as the reactive medium and additive are consumed and produce is formed. Thus, the color of the reaction mixture correlates to the amount of the product produced and the amount of reactive medium consumed. Further, the rate at which the reactive medium is consumed and the product is formed (e.g., a reaction rate) is a function of the additive concentration of the refrigerant and/or lubricant. Thus, color of the reaction mixture is a function of the reaction rate.

In an embodiment, the additive concentration of a lubricant and/or refrigerant may be determined in step 140 by comparing the color the reaction mixture determined in step 130 to a reference color. The reference color is the color of a reference reaction mixture. The reference reaction mixture is produced using a lubricant and/or refrigerant with a known additive concentration. The reference reaction mixture is produced utilizing similar conditions (e.g., reaction time, amount and type of reactive medium, type of additive(s)) as the reaction mixture, except with a known amount (e.g., concentration) of additive. Further, the color of the reaction mixture changes in a known manner. For example, in an embodiment, a product may be colored and the reactive medium may be colorless. In such an embodiment, the color of the reaction mixture increases (e.g., increases in intensity) as the reactive medium is consumed and the product is formed. The reaction mixture in such an embodiment may be compared to a reference color. If an intensity of color of the reaction mixture is greater than the reference color, the lubricant and/or refrigerant has a greater concentration of additive than the reference reaction mixture. If the intensity of the color of the reaction mixture is less than the reference color, the lubricant and/or refrigerant have a lesser concentration of additive than the reference reaction mixture.

In an embodiment, determination of the additive concentration of a lubricant and/or refrigerant in step 140 is based on one or more light reflecting properties of the reaction mixture. For example, the reaction mixture and the reactive medium can have one or more different light reflecting properties, such that one or more light reaction properties of the reaction mixture may be compared to a reference to determine an additive concentration of the lubricant and/or refrigerant. Further, in an embodiment, reference points (e.g., the percentage of light reflected using a specific light wavelength) may be calculated for one or more light reflecting properties by utilizing one or more reference reaction mixtures with a known additive concentration as similarly discussed above. Each reference point may be determined by testing a reference reaction mixture. Each reference point corresponds to a different amount of additive. In an embodiment, a reference point may be determined by measuring the light reflecting property (e.g., the percentage of light with a wavelength of 327 nm that is reflected) of a reference reaction mixture after being allowed to react for a specific period (e.g., the waiting period of step 120). In an embodiment, a reference point describes the light reflecting property (e.g., percentage of 327 nm light reflected) of the reaction mixture formed by reacting the lubricant and/or refrigerant with the minimum additive concentration for a set period (e.g., the waiting period in step 120). In an embodiment, a reference reaction mixture formed from a lubricant and/or refrigerant with no additive may be tested to determine a reference point corresponding to a lubricant and/or refrigerant with no additive. In an embodiment, a reactive mixture reflects more 327 nm light as the lubricant and/or refrigerant has an increased concentration of additive. Each reference point may correspond to a different additive concentration of the lubricant and/or refrigerant. The additive concentration of the refrigerant and/or lubricant in an embodiment is then determined in step 140 by comparing one or more of the light reflecting properties (e.g., percentage of light reflected at a specific wavelength) of the reaction mixture to one or more reference points.

In an embodiment, determination of the additive concentration of a lubricant and/or refrigerant in step 140 is based by color type of the reaction mixture. In an embodiment, a reaction mixture may need a minimum amount of product before a color change can be visually observed. The amount of the reactive medium and length of the waiting period of step 130 in an embodiment are configured so that the reaction mixture only has a visible change in color (relative to its color when first mixed) at step 130 if the additive concentration is greater than the minimum concentration. In such an embodiment, the reaction does not form the minimum amount of product in the time provided (e.g., the waiting period of step 120) to visibly change the color of the reaction mixture when the lubricant and/or refrigerant has an additive concentration is less than a minimum concentration. For example, the minimum concentration may be the minimum amount of additive needed for the additive to be effective in a refrigeration system (e.g., a HVACR system, the heat transfer circuit 1 in FIG. 1) or one or more of its components, as previously discussed.

In an embodiment, the amount of lubricant and/or refrigerant mixed with the reactive medium does not affect the amount of product produced when the color is determined (e.g., step 130) after reacting for a specific time (e.g., the waiting period in step 120) in an embodiment. This is advantageous as it may allow an operator (e.g., a field technician) to test a lubricant and/or refrigerant as described above without requiring an exact amount of lubricant and/or refrigerant to be measured while in the field.

In an embodiment, the method may not include waiting a specific amount of time (e.g., the waiting period of step 120) before determining the color of the reaction mixture (e.g., step 130). The color of the reaction mixture is utilized (e.g., step 140) in an embodiment to determining a reaction time. In an embodiment, the color of the reaction mixture is determined (e.g., step 130) and compared to a reference color or a reference point (as similarly discussed above) after mixing the lubricant and/or refrigerant. The color of the reaction mixture is determined (e.g., step 130) and compared until the color of the reaction is similar to a reference color or equal to or about equal to the reference point. The reaction time is the length of time between mixing the lubricant and/or refrigerant and the reactive medium (e.g., step 110) and the reactive mixture having a color similar to a reference color or a light reflecting property equal to or about equal to the reference point. The reaction time may then be compared to a reference reaction time. The reference reaction time is, for example, the amount of time (e.g., reaction time) for a lubricant and/or refrigerant containing the minimum concentration of additive to react with the reactive medium to form a reaction mixture with the reference color or a light reflecting property equal to or about equal to reference point. The reference reaction time may be determined by testing a reference reaction mixture as previously described.

In such an embodiment, an operator (e.g., a field technician) may take a sample of lubricant and/or refrigerant and mix it with the reactive mixture. The size of the sample (e.g., the amount of the lubricant and/or refrigerant) and the amount of reactive medium is similar to the reference sample. The operator may periodically or continuously determine the color of the reaction mixture (e.g., step 130) and compare the color of the reaction mixture to the reference color as it reacts. In an embodiment, the operator may periodically determine a light reflecting property of the reaction mixture (e.g., step 130) and compare the light reflecting property to a reference point. The operator measures the amount of time (e.g., the reaction time) that elapses between mixing lubricant and/or refrigerant and the reactive medium (e.g., step 110) and the reaction mixture having the color of the reference color or a light reflecting property equivalent to (e.g., at or about) the reference point. In an embodiment, step 140 includes comparing this amount of time (e.g., the reaction time) to the reference reaction time to determine the additive concentration of the lubricant and/or refrigerant. For example, in an embodiment, the additive concentration of the lubricant and/or refrigerant may be greater than the additive concentration of the lubricant and/or refrigerant utilized to form the reference reaction mixture when reaction time is less than the reference reaction time. In such an embodiment, the reference reaction mixture may have the minimum concentration of additive. Thus, in such an embodiment, the reaction time may be compared to the reference reaction time to determine an additive concentration of the lubricant and/or refrigerant. In particular, the additive concentration relative to the minimum concentration of additive may be determined (e.g., an additive concentration greater than the minimum concentration, an additive concentration less than the minimum concentration, an additive concentration approximately equal to the minimum concentration).

The reference color, the amount of reactive medium, and the size of the sample of lubricant and/or refrigerant may be selected as desired and/or suitable so as to allow an operator to quickly and accurately test for the additive concentration of a lubricant and/or refrigerant. For example, in an embodiment, the reference color, the amount of reactive medium, and the size of the sample of lubricant and/or refrigerant may be selected so that the reference reaction time is, for example, at or about 1 minute, at or about 10 minutes, at or about 15 minutes, or another time period at or about 1 minute to at or about 15 minutes.

In an embodiment, the concentration of an additive may not be constant throughout an entire refrigeration system (e.g. heat transfer circuit 1, HVACR system). As discussed above, a sample of refrigerant may be from a specific location along the heat transfer circuit 1 in an embodiment. This specific location may be referred to as a sampling location. In an embodiment, step 140 may include an adjustment factor based on the sampling location of the refrigeration system. The adjustment factor is a factor that adjusts the determined concentration of the additive in the sample to an adjusted concentration. The adjusted concentration may be, for example, the average concentration of an additive in the refrigerant and/or lubricant in the refrigeration system or a component (e.g., the compressor 2, the condenser 3, the expansion device 4, or the evaporator 5 in FIG. 1) of refrigeration system. For example, in an embodiment, it may be suitable and/or desired for working fluid flowing through the component to have at least a minimum amount of a particular additive. Accordingly, the adjustment factor may be utilized to determine if the component(s) of the refrigeration system have a refrigerant and/or lubricant with an additive concentration at or above their respective minimum additive concentration. For example, in an embodiment, the minimum concentration of epoxide additive in the condenser 3 may be at or about 50 ppm by weight, at or about 100 ppm by weight, at or about 200 ppm by weight, or a concentration at or about 50 ppm by weight to at or about 200 ppm by weight. For example, in an embodiment, the minimum concentration of hydrazone additive in the condenser 3 may be at or about 3 ppm by weight, at or about 80 ppm by weight, or a concentration at or about 3 ppm by weight to at or about 80 ppm by weight.

For example, a working fluid flowing through the condenser 3 may have an epoxide concentration of approximately 495 ppm by weight and the working fluid flowing through the evaporator 5 may have an average epoxide concentration of 950 ppm. In such an embodiment, the adjustment factor for determining the concentration of the epoxide additive in the working fluid of the evaporator 5 based on the sample taken at the condenser 3 is 1.92 (e.g., 950 ppm divided by 495 ppm). However, the adjustment factor and the concentration of an additive may be different depending upon the configuration of the refrigeration system in a particular embodiment.

In an embodiment, the additive concentration may not be constant throughout a component (e.g., the compressor 2, the condenser 3, the expansion device 4, or the evaporator 5 in FIG. 1) of the refrigeration system. The adjustment factor in an embodiment may include or be a factor that adjusts the determined additive concentration of the sample to the lowest concentration that occurs in the component based on where in the component the sample was taken from and how that location relates to the lowest concentration of additive in the condenser. In such an embodiment, the lowest concentration of additive is determined by using an adjustment factor to adjust the determined concentration of additive (e.g., the additive concentration determined in step 140) to the lowest concentration of additive that occurs in the same component or a different component of the refrigeration system.

Figure 3:
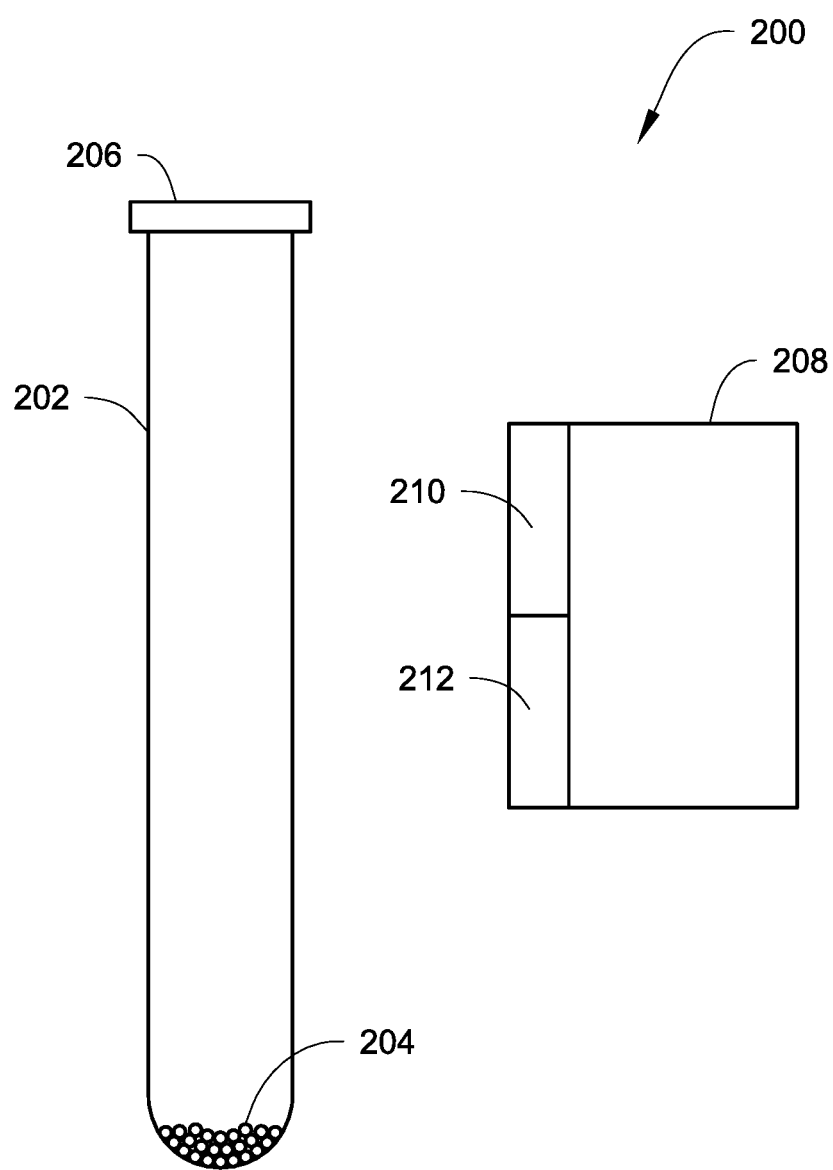
FIG. 3 shows a field testing device in an embodiment.

An embodiment of a field testing device 200 is shown in FIG. 3. The field testing device 200 includes a vessel 202. In an embodiment, the vessel 202 is a vial as shown in FIG. 3. However, the vessel 202 is not limited to a vial, and in other embodiments may have other shapes and/or configurations as is suitable and/or desired for use as a container, vessel, and the like.

The vessel 202 is configured to contain a reactive medium 204. Further, a liquid refrigerant and/or lubricant sample (not shown) is added to the vessel 202. The refrigerant and/or lubricant have an additive. The reactive medium 204 reacts with the additive to form a product with a different color than the reactive medium 204, as similarly discussed above. As discussed above, a color of the reaction mixture is related to the additive concentration of the lubrication and/or refrigerant sample as the color of reaction mixture is based on the amount of reactive medium 204 consumed and product formed. As discussed above, the color (e.g., the color type, color intensity, and/or light reflecting properties) of the reaction mixture may change after reacting for a specific time based on the additive concertation of the lubricant and/or refrigerant.

As discussed above, the additive for a lubricant and/or refrigerant in an embodiment may be an epoxide. In an embodiment, the reactive medium 204 is or includes hexavalent chromium (e.g., chromium (VI)). The hexavalent chromium reacts with the epoxide to form a chromium (III) complex. The chromium (III) complex has a different color than the reactive medium 204.

In an embodiment, the reactive medium 204 reacts with the additive for a lubricant and/or refrigerant to the form a quinone, as similarly discussed above. In such an embodiment, the reactive medium 204 may include a first reactant and a second react as discussed above. For example, in an embodiment, the reactive medium may include a Lewis acid (e.g., boron trifluoride ($BF_3$), aluminum fluoride ($AlF_3$), ammonia ($NH_3$)) as a first reactant and sulfuric acid and xylene as the second reactant. The quinone has a color that is different than the color of the reactive medium 204.

In an embodiment, the reactive medium 204 reacts with an epoxide additive to form a liquid product that has an orange color. In an embodiment, the reactive medium includes a first reactant and a second reactant. For example, in an embodiment, the reactive medium 204 may include 4-(p-nitrobenzyl)-pyridine as a first reactant and potassium acid phthalate as a second reactive.

As discussed above, an additive in a lubricant and/or a refrigerant is a hydrazone in an embodiment. In an embodiment, the reactive medium 204 reacts with the hydrazone additive to form a colored product. In an embodiment, the reactive medium 204 includes a first reactant and a second reactant. The first reactant reacts (e.g., hydrolyzes) with the hydrazone additive to form a hydrazine. The second reactant reacts with the hydrazine to form a colored (e.g., violet) product. For example, the first reactant may be a weak organic acid that can hydrolyze the additive hydrazone in the lubricant and/or refrigerant mixture to form a hydrazine. A weak organic acid may have, for example, a pH equal to or greater than 3 and less than 7. For example, in an embodiment, the reactive medium 204 may include an alkali and salicladehyde as the second reactant.

However, it should be appreciated that the reactive medium 204 is not limited to the listed chemical substances (e.g., hexavalent chromium, sulfuric acid, xylene, 4-(p-nitrobenzyl)-pyridine, potassium acid phthalate, an alkali, salicladehyde, boron trifluoride ($BF_3$), aluminum fluoride ($AlF_3$), ammonia ($NH_3$)) described herein. A reactive medium 204 may include other chemical substances that react with an additive to form a product having a different color than the reactive medium 204.

As shown in FIG. 3, the vessel 202 includes a removable cover 206 for sealing the vessel 202. The cover 206 allows for the reactive medium 204 to be sealed within the vessel 202 during storage and transportation. The cover 206 can prevent the reaction mixture 204 from spilling from the vessel 202 when the reactive medium 204, product, the lubricant, and/or refrigerant present a regulatory or environmental concern. For example, a regulatory or environmental concern may be that the reactive medium 204, the product, a lubricant, or a refrigerant is a hazardous substance.

The reactive medium 204 is shown as beads in FIG. 3. The reactive medium 204 is a coating on an inert bead. However, the reactive medium 204 in an embodiment may be attached to another material. In an embodiment, the reactive medium may be powder comprising very small coated beads. In an embodiment, the reactive medium may be a liquid. The liquid reactive medium in an embodiment may react with an additive to form a colored liquid product, a precipitate, or a colored precipitate. In an embodiment with a mixing of the liquid reactive medium and/or liquid product with the lubricant and/or refrigerant may affect the color of the reactive mixture. Accordingly, a reference color may account for any effect caused by the liquid reactive medium and/or liquid product mixing with the lubricant and/or refrigerant.

The field testing device 200 may also include a color indicator 208 in an embodiment. The color indicator 208 as shown has two colors 210, 212. However, the color indicator 208 in an embodiment may include one or more colors 210, 212. In an embodiment, the color indicator 208 may include a spectrum of color intensities. Each color 210, 212 corresponds to a specific concentration of the additive. For example, the first color 210 in an embodiment may correspond to concentration of 50 ppm by weight. Accordingly, if the intensity of the color of the reaction mixture is equal to or greater than the first color 210, the additive concentration of the lubricant and/or refrigerant is equal to or greater than 50 ppm by weight. The second color 212 may similarly indicate a second additive concentration for the lubricant and/or refrigerant. The color indicator 208 is separate from the vessel 202 in the illustrated embodiment. However, in an embodiment, the color indicator 208 may be included as a part of the vessel 202. In an embodiment, the field testing device 200 may not include a color indicator 208. In such an embodiment, the reaction mixture after being allowed to react for a specific time may not visibly change color (relative to its color when first mixed) below a minimum concentration of additive as discussed above. Thus, a color indicator 208 may not be included in an embodiment as any visible color change indicates a sufficient amount (e.g., an amount equal to or greater than the minimum concentration)

of additive is present in the lubricant and/or refrigerant. In an embodiment, a spectrophotometer (not shown) may be utilized to determine the one or more of light reflecting properties of the reaction mixture, as similarly described above.

Figure 4:
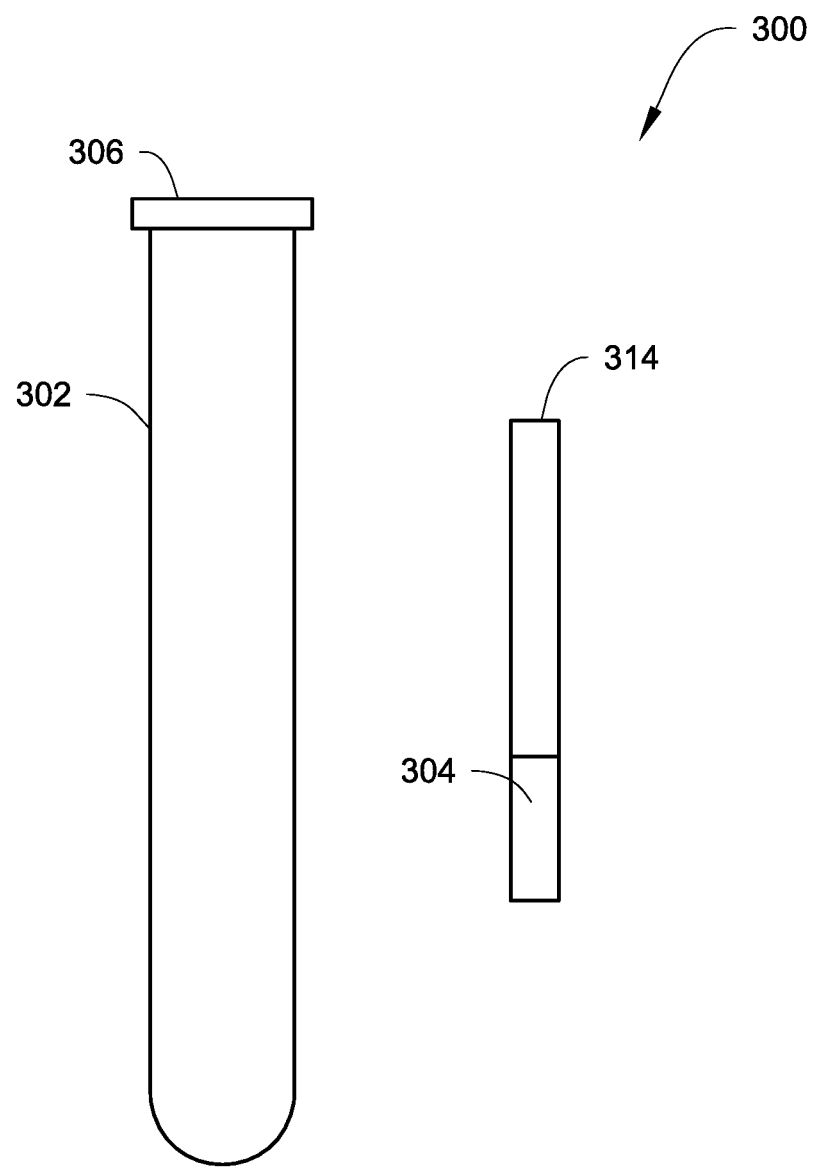
FIG. 4 shows a field testing device in an embodiment.

An embodiment of a field testing device 300 is shown in FIG. 4. The field testing device includes a cap 306 and vial 302 similar to the cap 206 and vial 202 shown in FIG. 3 and discussed above. The field testing device 300 also includes a test strip 314. The test strip 314 includes a reactive medium 304 that covers a lower portion of the test strip 314. The reactive medium 304 covers a lower portion of the test strip 314, but in an embodiment the entire test strip 314 may be covered with the reactive medium. The test strip 314 is shown outside the vial 302 in FIG. 4. However, the test strip 314 may attached to inside of the vial in an embodiment.

The reactive medium 304 may have a similar composition to the reactive medium 204 shown in FIG. 3 and as discussed above. In an embodiment, the reactive medium 304 is mixed with a lubricant and/or refrigerant by dipping the test strip 314 into the lubricant and/or refrigerant that is located in the vial 302. In an embodiment, the test strip 314 may have one or more colored portions. For example, the test strip 314 may have one or more colored portions that correspond to a specific concentration of additive, similar to the colors 210, 212 of the color indicator 208 of the field testing device 200 in FIG. 3. For example, the colored portions may be located on the portion of the test strip 314 that is not covered by the reactive medium 304. In an embodiment, the field testing device 300 may include a color indicator similar to the color indicator 208 shown in FIG. 3 and as described above.

In an embodiment, field testing device 200, 300 may be implemented in the method shown in FIG. 2 and as described above to detect an additive in a lubricant and/or refrigerant mixture. For example, in an embodiment, a field technician may operate the field testing device according to the method to determine the concentration of the lubricant and/or refrigerant of a refrigeration system (e.g., a HVACR system, the heat transfer circuit 1 in FIG. 1). The field testing device 200, 300 is small enough to be easily portable (e.g., easily carried/transported) by a field technician in the field. The portability of the field testing device 200, 300 allows the field technician to easily carry the field testing device 200, 300 to the refrigeration system.

A refrigeration system is located in the field (e.g., not at a laboratory or testing facility). For example, a location of the refrigeration system in an embodiment may be a commercial building, a residential house, or other similar building that includes a refrigeration system for heating and/or cooling. A refrigeration system requires servicing by a field technician. For example, the field technician may service the refrigeration system to examine the refrigeration system, perform routine maintenance, repair a refrigeration system, and/or configure a newly installed refrigeration system. When servicing a refrigeration system, the field technician may need to determine if the lubricant and/or refrigerant includes an adequate amount of additive. The refrigeration system may, for example, operate at a reduced efficiency if the lubricant and/or refrigerant do not include an adequate amount (e.g., a minimum concentration of additive as discussed above) of additive. The portability of the field testing device 200 is advantageous as it allows the field technician to quickly and accurately test and determine the additive concentration of a refrigerant and/or lubricant at the refrigeration system without requiring the field technician to leave the refrigeration system and/or send a sample to a laboratory. In an embodiment, the field technician may add additive(s) to the lubricant and/or refrigerant of the refrigeration system and utilize the field testing device 200 to determine if enough additive(s) has been added. As the operator can perform the testing at while at the location of the refrigeration system, the operator may make any adjustments to the refrigeration system (e.g., adding additional additive) before leaving that location.

Aspects:

Any of aspects 1-15 can be combined with any of aspects 16-24.

Aspect 1. A method for operating a field testing device to detect an additive in a refrigerant, a lubricant, or a refrigerant and lubricant mixture, the refrigerant, lubricant, or refrigerant and lubricant mixture being utilized by a refrigeration system, the field testing device comprising a vessel and a reactive medium, the reactive medium being configured to react with an additive to form a product, the product having a different color than the reactive medium, the method comprising:

mixing, in the vessel, the reactive medium with a sample of the refrigerant, lubricant, or refrigerant and lubricant mixture at a location of the refrigeration system;

determining a color of a reaction mixture at the location of the of the refrigeration system, the reaction mixture including one or more of the product and the reactive medium; and utilizing the color of the reaction mixture to determine an additive concentration of the refrigerant, lubricant, or refrigerant and lubricant mixture at the location of the of the refrigeration system.

Aspect 2. The method of aspect 2, further comprising:

waiting a specific amount of time between mixing the reactive medium with a sample of the refrigerant, lubricant, or refrigerant and lubricant mixture and determining a color of a reaction mixture, wherein utilizing the color of the reaction mixture to determine the additive concentration of the refrigerant, lubricant, or refrigerant and lubricant mixture is based on the waiting period.

Aspect 3. The method of either of aspects 1 or 2, wherein the color of reaction mixture and a color of the reactive medium are the same when the additive concentration of the refrigerant, lubricant, or refrigerant and lubricant mixture is less than a minimum additive concentration.

Aspect 4. The method of any of aspects 1-3, wherein utilizing the color of the reaction mixture to determine the additive concentration of the refrigerant, lubricant, or refrigerant and lubricant mixture includes comparing the color of the reaction mixture with a reference color.

Aspect 5. The method of aspect 4, wherein utilizing the color of the reaction mixture to determine the additive concentration of the refrigerant, lubricant, or refrigerant and lubricant mixture further includes:

determining a reaction time, the reaction time being an amount of time between mixing the reactive medium with a sample of the refrigerant, lubricant, or refrigerant and lubricant mixture and the color of the reactive mixture being similar to the reference color, comparing the reaction time to a reference reaction time to determine the additive concentration of the refrigerant, lubricant, or refrigerant and lubricant mixture.

Aspect 6. The method of either of aspects 1 or 2, wherein determining the color of the reaction mixture includes determining a light reflecting property of the reaction mixture, and utilizing the color of the reaction mixture to determine the additive concentration of the refrigerant, lubricant, or refrigerant and lubricant mixture includes comparing the light reflecting property to one or more reference points.

Aspect 7. The method of aspect 6, wherein utilizing the color of the reaction mixture to determine the additive concentration of the refrigerant, lubricant, or refrigerant and lubricant mixture further includes:

determining a reaction time, the reaction time being an amount of time between mixing the reactive medium with a sample of the refrigerant, lubricant, or refrigerant and lubricant mixture and the light reflecting property of the reactive mixture being at or about one of the one or more reference points, comparing the reaction time to a reference reaction time to determine the additive concentration of the refrigerant, lubricant, or refrigerant and lubricant mixture.

Aspect 8. The method of any of aspects 1-7, wherein the additive is an epoxide.

Aspect 9. The method of any of aspects 1-8, wherein the reactive medium includes hexavalent chromium.

Aspect 10. The method of any of aspects 1-8, wherein the product is a quinone.

Aspect 11. The method of aspects 1-8, wherein the reactive medium includes 4-(p-nitrobenzyl)-pyridine and potassium acid phthalate.

Aspect 12. The method of any of aspects 1-7, wherein the additive is a hydrazone.

Aspect 13. The method of any of aspects 1-12, wherein the reactive medium is located on one or more inert beads.

Aspect 14. The method of any of aspects 1-12, wherein the reactive medium is located on a test strip, and mixing the reactive medium with the sample of the refrigerant, lubricant, or refrigerant and lubricant mixture includes inserting the reactive medium on the test strip into the sample of the refrigerant, lubricant, or refrigerant and lubricant mixture.

Aspect 15. A method for determining an additive concentration of a working fluid in a refrigeration system, the method comprising:

taking a sample of a working fluid of the refrigeration system, and determining an additive concentration of the sample of the working fluid by the method of aspect 1, and determining an additive concentration in a component of the refrigeration system by utilizing the additive concentration of the sample of the working fluid and an adjustment factor, the adjustment factor being based on a sampling location.

Aspect 16. A portable field testing device for detecting an additive in a refrigerant, a lubricant, a refrigerant and lubricant mixture in the field, the field testing device comprising:

a vessel configured to hold the refrigerant, lubricant, or refrigerant and lubricant mixture; and a reactive medium that reacts to the additive in the refrigerant or the lubricant to form a product, a color of the product being different than a color of the reactive medium, and the color of the product is configured to correspond to a concentration of the additive in the refrigerant or lubricant, wherein the portable field testing device is configured to determine a concentration of the additive in the refrigerant in the field.

Aspect 17. The field testing device of aspect 16, further comprising:

a color indicator including one or more colors, each of the one or more colors corresponding to a specific concentration of additive in the refrigerant or lubricant.

Aspect 18. The field testing device of either of aspects 16 or 17, further comprising:

one or more inert beads, wherein the reactive medium is located on the one or more inert beads.

Aspect 19. The field testing device of either of aspects 16 or 17, further comprising:

a test strip, wherein the reactive medium is located on the test strip.

Aspect 20. The field testing device of any of aspects 16-19, wherein the additive is an epoxide.

Aspect 21. The field testing device of any of aspects 16-20, wherein the reactive medium includes hexavalent chromium.

Aspect 22. The field testing device of any of aspects 16-20, wherein the product is a quinone.

Aspect 23. The field testing device of any of aspects 16-20, wherein the reactive medium includes 4-(p-nitrobenzyl)-pyridine and potassium acid phthalate.

Aspect 24. The field testing device of any of aspects 16-19, wherein the additive is a hydrazone.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

What is claimed is:

1. A method for operating a field testing device to detect an additive in a refrigerant, a lubricant, or a refrigerant and lubricant mixture, the refrigerant, lubricant, or refrigerant and lubricant mixture being utilized by a refrigeration system, and the additive being a composition previously added to the refrigeration system to enhance performance of the refrigerant or the lubricant when the additive is at least at a minimum additive concentration, the field testing device comprising a vessel and a reactive medium, the reactive medium being configured to react with an additive to form a product, the product having a different color than the reactive medium, the method comprising: mixing, in the vessel, the reactive medium with a sample of the refrigerant, lubricant, or refrigerant and lubricant mixture at a location of the refrigeration system; determining a color of a reaction mixture at a location of the refrigeration system, the reaction mixture including one or more of the product and the reactive medium; and utilizing the color of the reaction mixture to determine an additive concentration of the refrigerant, lubricant, or refrigerant and lubricant mixture at the location of the refrigeration system.

2. The method of claim 1, further comprising:

waiting a specific amount of time between mixing the reactive medium with a sample of the refrigerant, lubricant, or refrigerant and lubricant mixture and determining a color of a reaction mixture, wherein utilizing the color of the reaction mixture to determine the additive concentration of the refrigerant, lubricant, or refrigerant and lubricant mixture is based on the waiting period.

3. The method of claim 2, wherein the color of reaction mixture and a color of the reactive medium are the same when the additive concentration of the refrigerant, lubricant, or refrigerant and lubricant mixture is less than the minimum additive concentration.

4. The method of claim 1, wherein utilizing the color of the reaction mixture to determine the additive concentration of the refrigerant, lubricant, or refrigerant and lubricant mixture includes comparing the color of the reaction mixture with a reference color.

5. The method of claim 4, wherein utilizing the color of the reaction mixture to determine the additive concentration of the refrigerant, lubricant, or refrigerant and lubricant mixture further includes:
determining a reaction time, the reaction time being an amount of time between mixing the reactive medium with a sample of the refrigerant, lubricant, or refrigerant and lubricant mixture and the color of the reactive mixture being similar to the reference color,
comparing the reaction time to a reference reaction time to determine the additive concentration of the refrigerant, lubricant, or refrigerant and lubricant mixture.

6. The method of claim 1, wherein
determining the color of the reaction mixture includes determining a light reflecting property of the reaction mixture, and
utilizing the color of the reaction mixture to determine the additive concentration of the refrigerant, lubricant, or refrigerant and lubricant mixture includes comparing the light reflecting property to one or more reference points.

7. The method of claim 6, wherein utilizing the color of the reaction mixture to determine the additive concentration of the refrigerant, lubricant, or refrigerant and lubricant mixture further includes:
determining a reaction time, the reaction time being an amount of time between mixing the reactive medium with a sample of the refrigerant, lubricant, or refrigerant and lubricant mixture and the light reflecting property of the reactive mixture being at or about one of the one or more reference points,
comparing the reaction time to a reference reaction time to determine the additive concentration of the refrigerant, lubricant, or refrigerant and lubricant mixture.

8. The method of claim 1, wherein the additive is an epoxide.

9. The method of claim 1, wherein the reactive medium includes hexavalent chromium.

10. The method of claim 1, wherein the product is a quinone.

11. The method of claim 1, wherein the reactive medium includes 4-(p-nitrobenzyl)-pyridine and potassium acid phthalate.

12. The method of claim 1, wherein the additive is a hydrazone.

13. The method of claim 1, wherein the reactive medium is located on one or more inert beads.

14. The method of claim 1, wherein
the reactive medium is located on a test strip, and
mixing the reactive medium with the sample of the refrigerant, lubricant, or refrigerant and lubricant mixture includes inserting the reactive medium on the test strip into the sample of the refrigerant, lubricant, or refrigerant and lubricant mixture.

15. A method for determining an additive concentration of a working fluid in a refrigeration system, the method comprising:
taking a sample of a working fluid of the refrigeration system, and
determining an additive concentration of the sample of the working fluid by the method of claim 1, and
determining an additive concentration in a component of the refrigeration system by utilizing the additive concentration of the sample of the working fluid and an adjustment factor, the adjustment factor being based on a sampling location.

16. A method for operating a field testing device to detect an additive in a refrigerant, a lubricant, or a refrigerant and lubricant mixture, the refrigerant, lubricant, or refrigerant and lubricant mixture being utilized by a refrigeration system,
the field testing device comprising a vessel and a reactive medium, the reactive medium being located on one or more inert beads and configured to react with an additive to form a product, the product having a different color than the reactive medium,
the method comprising:
mixing, in the vessel, the one or more inert beads having the reactive medium with a sample of the refrigerant, lubricant, or refrigerant and lubricant mixture at a location of the refrigeration system;
determining a color of a reaction mixture at a location of the refrigeration system, the reaction mixture including one or more of the product and the reactive medium; and
utilizing the color of the reaction mixture to determine an additive concentration of the refrigerant, lubricant, or refrigerant and lubricant mixture at the location of the refrigeration system.

17. A method for operating a field testing device to detect an additive in a refrigerant, a lubricant, or a refrigerant and lubricant mixture, the refrigerant, lubricant, or refrigerant and lubricant mixture being utilized by a refrigeration system,
the field testing device comprising a vessel and a reactive medium, the reactive medium being located on a test strip and configured to react with an additive to form a product, the product having a different color than the reactive medium,
the method comprising:
mixing, in the vessel, the reactive medium with a sample of the refrigerant, lubricant, or refrigerant and lubricant mixture at a location of the refrigeration system, wherein mixing the reactive medium with the sample of the refrigerant, lubricant, or refrigerant and lubricant mixture includes inserting the reactive medium on the test strip into the sample of the refrigerant, lubricant, or refrigerant and lubricant mixture;
determining a color of a reaction mixture at a location of the refrigeration system, the reaction mixture including one or more of the product and the reactive medium; and
utilizing the color of the reaction mixture to determine an additive concentration of the refrigerant, lubricant, or refrigerant and lubricant mixture at the location of the refrigeration system.

* * * * *